United States Patent [19]
Hellstrom et al.

[11] Patent Number: 5,165,922
[45] Date of Patent: Nov. 24, 1992

[54] SYNERGISTIC TUMOR THERAPY WITH COMBINATIONS OF BIOLOGICALLY ACTIVE ANTI-TUMOR ANTIBODIES AND CHEMOTHERAPY

[75] Inventors: Karl E. Hellstrom; Ingegerd Hellstrom, both of Seattle; Gary E. Goodman, Bellevue, all of Wash.

[73] Assignee: Bristol-Myers Squibb Company, New York, N.Y.

[21] Appl. No.: 527,227

[22] Filed: May 22, 1990

[51] Int. Cl.$^5$ .................. A61K 39/395; C07K 15/28; C12P 21/08; C12N 15/02
[52] U.S. Cl. .................. 424/85.8; 530/388.8; 435/70.21; 435/172.2
[58] Field of Search .................. 424/85.8; 530/388.8; 435/172.2, 70.21

[56] References Cited

U.S. PATENT DOCUMENTS
4,693,966 9/1987 Houghton et al. .................. 435/7

OTHER PUBLICATIONS

Abowd-Piral, E. et al., J. Natl. Cancer Inst., 80:1605-1611, 1988.
Kannagi, R. et al., Handbook of Experimental Immunology, vol. 4, Chap. 117, pp. 117.1-117.20, 1986.
Vadhan-Raj et al., 1988, J. Clin. Oncol. 6 (No. 10): 1636-1648.
Vitetta et al., 1984, Transplantation 37 (No. 6): 535-538.
Webb et al., 1986, Cancer Immunol. Immunother. 21: 100-106.
Yeh et a., 1982, Int. J. Cancer 29: 269-275.
Goodman et al., 1985, J. Clin. Oncol. 3 (No. 3): 340-352 ("Goodman I").
Goodman et al., 1988, Proc. Annu. Meet. Am. Assoc. Cancer Res. 29: A733 ("Goodman II").
Hellstrom et al., in Accomplishments In Cancer Research—1984 Prize Year, General Motors Cancer Research Foundation, Fortner et al. (eds.), pp. 216-238 (J. B. Lippincott Company, Philadelphia 1985) ("Hellstrom I").
Hellstrom et al., 1985, Proc. Natl. Acad. Sci. USA 82: 1499-1502 ("Hellstrom II").
Hellstrom et al., Aug. 1986, Cancer Res. 46: 3917-3923 ("Hellstrom III").
Hellstrom et al., Sep. 1986, Proc. Natl. Acad. Sci. USA 83: 7059-7063 ("Hellstrom IV").
Hellstrom et al., in Covalently Modified Antigens And Antibodies in Diagnosis And Therapy, Quash et al. (eds.), pp. 1-39 (Marcel Dekker, Inc. New York 1989) ("Hellstrom V").
Houghton et al., 1985, Proc. Natl. Acad. Sci. USA 82: 1242-1246.
Hurwitz et al., 1986, Int. J. Cancer 37: 739-745.
Key et al., 1983, J. Immunol. 130 (No. 6): 2987-2992.
Kokoschka et al., 1977, Wien Klin Wochenschr 89 (18): 612-622. (Abstract in English).
Koprowski et al., in Monoclonal Antibodies And T--Cell Hybridomas, Hammerling et al. (eds.), pp. 161-173 (Elsevier/North-Holland Biomedical Press 1981).
Lanier et al., 1979, J. Natl. Cancer Instit. 63 (No. 6): 1417-1422.
Modha et al., 1990, Parasite Immunology 12: 321-334.
Okabe et al., 1985, Jap. J. Med. 24 (No. 3): 250-256.
Order, 1984, Comprehensive Therapy 10(1): 9-18.
Sears et al., Lancet, Apr. 3, 1982: 762-765 ("Sears I").
Sears et al., 1985, Cancer Res. 45: 5910-5913 ("Sears II").
Shapiro et al., 1982, Cancer Res. 42: 2622-2627.
Shearer et al., 1984, Immunopharmacology 8: 103-110.
Steplewski et al., 1986, Recent Results in Cancer Research 100: 321-323.
Brown et al., 1981, J. Immunol. 127 (No. 2): 539-546.
Burchell et al., in Monoclonal Antibodies For Cancer Detection And Therapy, R. W. Baldwin et al. (eds.), pp. 1-15 (Academic Press 1985).
Carrasquillo et al., 1984, Cancer Treatment Reports 68 (No. 1): 317-328.
Chen et al., 1989, J. Immunol. 143 (No. 3): 1053-1057.
Dippold et al., 1980, Proc. Natl. Acad. Sci. USA 77: 6114-6118.
Doenhoff et al., 1988, Immunology 65: 507-510.
Ghose et al., 1972, British Medical Journal 26: 495-499.

*Primary Examiner*—Esther L. Kepplinger
*Assistant Examiner*—Susan L. Futrovsky
*Attorney, Agent, or Firm*—Pennie & Edmonds

[57] ABSTRACT

The present invention relates to the use of combinations of antibody therapy and chemotherapy in the treatment of malignant disease. More particularly, the invention relates to novel methods of treating patients who have malignant disease and who have shown an unresponsiveness to treatment with standard chemotherapy regimens by administering to those patients (i) an antibody that binds to the malignant cells of the patient and (ii) a chemotherapeutic agent. According to particular embodiments of the invention, anti-glycolipid antibodies are administered to patients who are subsequently treated with standard chemotherapy regimens.

2 Claims, No Drawings

SYNERGISTIC TUMOR THERAPY WITH COMBINATIONS OF BIOLOGICALLY ACTIVE ANTI-TUMOR ANTIBODIES AND CHEMOTHERAPY

FIELD OF THE INVENTION

The present invention relates to the use of combinations of antibody therapy and chemotherapy in the treatment of malignant disease. It is based, in part, on the surprising discovery that patients previously unresponsive to standard chemotherapy regimens achieved complete remission when treated with a combination regimen comprising treatment with anti-tumor antibody as well as chemotherapy. The methods of the invention provide a unique means for marshalling a patient's immune system to act in concert with exogenous chemical compounds to effectively eradicate tumor cells.

BACKGROUND OF THE INVENTION

TUMOR CELL ANTIGENS AND ANTI-TUMOR ANTIBODIES

Tumor cells express certain antigens which are absent from, or present in small amounts on, their normal cellular counterparts. Most of these are differentiation antigens, shared by the tumor and certain embryonic cells. Some of the antigens that appear with sufficient selectivity in tumors may serve as possible targets for therapeutic agents. This has been recently reviewed for malignant melanoma, which is one of the human tumors most studied in this respect (Hellstrom and Hellstrom, in Accomplishments in Cancer Research-194 Prize Year, General Motors Cancer Research Foundation, J. G. Fortner & J. E. Rhoads, eds., J. B. Lippincott Company, Philadelphia 1985, p. 216-240), as well as for other tumors (Burchell and Taylor-Papadimitriou, in R. W. Baldwin and V. S. Byers, eds., Monoclonal Antibodies for Tumor Detection and Drug Targeting, Academic Press, 1985, pp. 1-15; Kemshead, ibid, pp. 281-302).

Many antibodies have been made to cell surface antigens that are expressed in greater quantities by human tumors than by normal tissues. It has also been well established that antibodies to cell surface antigens can be cytotoxic to tumor cells in the presence of complement (Hellstrom et al., 1962, Progr. Allergy 9: 158-245), and that some antibodies can mediate antibody-dependent cellular cytotoxicity (Perlmann et al., 1969, Adv. Immunol. 11: 117-193; MacLennan et al., 1969, Immunol. 17: 897-910; Skurzak et al., 1972, J. Exp. Med. 135: 997-1002; Pollack et al., 1972, Int. J. Cancer, 9: 316-323). In the first case, an appropriate source of complement (generally rabbit or guinea pig), and in the latter case a source of effector cells (generally of mouse origin) is needed.

The evidence that antibodies to tumor-associated antigens can kill human tumor cells in the presence of human effector cells is more recent (Hellstrom et al., 1981, Int. J. Cancer 27: 281-285) as is the evidence that antibodies to such antigens can kill tumor cells in the presence of human serum as a source of complement (Hellstrom et al., 1985, Proc. Natl. Acad. Sci. 82: 1499-1502; Hellstrom et al., 1985, Monoclonal Antibodies and Cancer Therapy, USCLA Symposia on Molecular and Cellular Biology, Vol. 27, pp. 149-164 Alan R. Liss, Inc., NY).

THERAPEUTIC USES OF ANTI-TUMOR ANTIBODIES AS CARRIERS OF RADIOISOTOPES, TOXINS OR DRUGS

Attractive approaches for preparing anti-cancer agents involve labeling antibodies with radioactive isotopes (Larson et al., 1983, J. Clin. Invest. 72: 2101-2114; Order, 1984, Compr. Ther. 10: 9-18; Carrasquillo et al., 1984, Cancer Treatment Reports 68: 317-328; de Nardo et al. 1985, Int. J. Radiation Oncology Biol. Phys. 11: 335-348), or conjugating antibodies to toxins (Jansen et al., 1982, Immunol. Rev. 62: 185-216; Vitetta and Uhr, 1984, Transplant. 7: 535-538) or anti-cancer drugs (Ghose et al., 1972, Brit. Med. J. 3: 495-499; Hurwitz et al., 1975, Cancer Res. 35: 1175-1181; Rowland et al., 1985, Cancer Immunol. Immunother. 1-7). The antibody gives the specificity and the isotope or drug provides the ability to destroy the tumor. However, a disadvantage of this approach is the fact that both anti-cancer drugs and radioisotopes have a high level of toxicity to normal tissues. Thus, nonspecific uptake in various organs such as kidney, liver, or bone-marrow could lead to substantial side-effects.

SUMMARY OF THE INVENTION

The present invention relates to the use of combinations of antibody therapy and chemotherapy in the treatment of malignant disease. It is based in part, on observations of the surprising effectiveness of combination therapy; several patients who had received the anti-tumor antibody L6 or MG21 achieved complete remission in response to subsequent chemotherapy, although the same patients had not responded to similar chemotherapy regimens prior to receiving L6 or MG21 antibody treatment.

In particular embodiments of the invention, anti-glycolipid antibodies such as, preferably, L6 monoclonal antibody or MG21 monoclonal antibody, are administered to patients who are subsequently treated with standard chemotherapy regimens. In preferred embodiments of the invention, chemotherapy is administered within several months of antibody treatment. It is suggested that the effectiveness of combination therapy can be attributable to antibodies at the tumor site which render the malignant cells more susceptible to the toxic effects of chemotherapeutic agents or induce an immune response in a patient that synergizes with the chemotherapy drugs.

DETAILED DESCRIPTION OF THE INVENTION

The present invention relates to therapeutic regimens comprising treatment with anti-tumor antibodies and standard chemotherapy. In preferred embodiments of the invention, the anti-tumor antibodies react with glycolipid antigens on the surface of tumor cells. In most preferred embodiments, the anti-tumor antibody is the monoclonal antibody L6 or the monoclonal antibody MG21.

Although there is no duty to explain the efficacy of antibody/chemotherapy regimens in tumor cell killing, several mechanisms may be involved. First, it has been observed that the anti-tumor antibodies L6 and MG21 are present at the tumor site weeks after administration. By binding to the surface of tumor cells, the antibodies may render the cells more susceptible to chemotherapeutic killing, possibly by increasing drug uptake. Alternatively, treatment with anti-tumor antibody may induce an immune response in patients which synergizes with the chemotherapy drugs, either by making the cells more sensitive to the drugs or by making the cells more sensitive to the patient's immune response.

For purposes of clarity of disclosure, and not by way of limitation, the detailed description of the invention will be divided into the following subsections:
(i) characteristics of the antibody molecules of the invention;
(ii) preparation of monoclonal antibodies; and
(iii) tumor therapy with combinations of biologically active anti-tumor antibodies and chemotherapy.

CHARACTERISTICS OF THE ANTIBODY MOLECULES OF THE INVENTION

Antibodies of virtually any origin can be used according to the present invention, but in preferred embodiments the antibodies define a tumor-associated antigen, such as a glycolipid antigen, a glycoprotein antigen, or mucin. Monoclonal antibodies offer the advantage of a continuous, ample supply. In fact, by immunizing mice with tumor-associated glycolipid antigens establishing hybridomas making antibodies to such antigens it should be possible to rapidly establish a panel of antibodies capable of reacting with and treating a large variety of human tumors.

The MG21 antibody is also described in copending U.S. application Ser. No. 834,162 filed Feb. 20, 1986 which is incorporated by reference herein. The L6 antibody and the antigen it defines are described more fully in copending U.S. application Ser. No. 684,759, now U.S. Pat. No. 4,935,495, filed Dec. 21, 1984 and in U.S. Pat. No. 4,906,562, filed Oct. 18, 1985 which are each incorporated by reference herein.

PREPARATION OF MONOCLONAL ANTIBODIES

According to the invention, monoclonal antibodies can be produced using any method known in the art, including but not limited to the hybridoma technique originally developed by Kohler and Milstein (1975, Nature 256: 495-497) as well as the trioma technique, the human B-cell hybridoma technique (Kozborn et al., 1983, Immunology Today 4: 72), the EBV-hybridoma technique (Cole et al., 1985, in "Monoclonal Antibodies and Cancer Therapy," Alan R. Liss, Inc. pp. 77-96), and Huse et al., 1989, Science 246: 1275-1281, as well as the chimeric antibody techniques discussed infra.

While the invention is demonstrated using mouse monoclonal antibodies, the invention is not so limited; in fact, human antibodies can be used and may prove to be preferable. Such antibodies can be obtained by using human hybridomas (Cote et al., 1983, Proc. Natl. Acad. Sci., 80: 2026-2030) or by transforming human B cells with EBV virus in vitro (Cole et al., 1985, in, Monoclonal Antibodies and Cancer Therapy, Alan R. Liss, pp. 77-96). In fact, according to the invention, techniques developed for the production of "chimeric antibodies" (Morrison et al., 1984, Proc. Natl. Acad. Sci., 81: 6851-6855; Neuberger et al., 1984, Nature 312: 604-608; Takeda et al., 1985, Nature 314: 452-454) by splicing the genes from a mouse antibody molecule of appropriate antigen specificity together with genes from a human antibody molecule of appropriate biological activity can be used.

The subsections below describe how the antibodies used in the examples which follow were prepared.

The binding assays used to characterize the specificity of the antibodies were performed by using radiolabeled antibodies (Brown et al., 1981, Proc. Natl. Acad. Sci. 78: 539-543); cultured cells ($10^6$) were incubated at 4° C. for 30 minutes with $10^6$ cpm of $^{125}$I-labeled antibody in 100 μl of heat-inactivated (30 minutes at 56° C.) fetal calf serum in culture medium. After the addition of 5 ml of PBS, the cells were pelleted by centrifugation for 10 minutes at 250×g. The supernatant was aspirated and the pellet was assayed for $^{125}$I. To measure nonspecific binding, parallel incubations were performed with 10 μg of unlabeled antibody as a competitor (Brown et al., 1981, Proc. Natl. Acad. Sci. 78: 539-543). In some instances binding assays were carried out in an analogous fashion on cell monolayers attached to plastic culture dishes.

MONOCLONAL ANTIBODIES DIRECTED AGAINST MELANOMA GLYCOLIPIDS

In order to prepare antibodies directed against tumor-associated glycolipid antigens of melanoma cells, BALB/c mice were immunized with a melanoma cell line, SK-MEL-28, and their spleen cells subsequently were hybridized with NS-1 cells. Hybridoma supernatants were screened for binding to GD3 that had been isolated from melanoma tissue and attached to the surface of the wells of Falcon 3034 Microtest plates as previously described (Yeh et al., 1982, Int. J. Cancer 29: 269-275). Irrelevant gangliosides were included as controls. Hybridomas 2B2 and IF4 were derived from one hybridization, and hybridoma MG21, from a different one. They were cloned twice by limiting dilution; all make antibodies that are IgG3 according to gel diffusion.

Antibodies were affinity-purified on a column of staphylococcal protein A covalently linked to Sepharose CL-4B (Pharmacia) by elution with 0.1M citrate buffer, pH 3.5 or 4.5 (Brown et al., 1981, J. Immunol. 127: 539-546).

Antibody specificity for melanoma was established by binding assays with cultured cells, as published for antibody 4.2. (Yeh et al., 1982, Int. J. Cancer 29: 269-275; Nudelman et al., 1982, J. Biol. Chem. 257: 12752-12756). Specificity was confirmed by immunohistological studies on frozen section (Garrigues et al., 1982, Int. J. Cancer 29: 511-515), in which antibodies 2B2, IF4, and MG21 stained samples from approximately 80% of metastatic melanomas, whereas normal tissues, including kidney and brain, were not stained; the specificity data for 2B2 have been published (Hellstrom et al., 1984, Contributions to Oncology Series: Genes and Antigens in Cancer Cells, eds. Riethmuller, G., Koprowski, H., Van Kliest, S. & Munk, K. (Karger, Basel), pp. 121-131.

MONOCLONAL ANTIBODIES DIRECTED AGAINST NON-SMALL CELL LUNG CARCINOMA GLYCOLIPID

The L6 monoclonal antibody was prepared as previously described in copending U.S. application Ser. No. 684,759 filed Dec. 21, 1984 and in U.S. Pat. No. 4,906,562 filed Oct. 18, 1985 each of which is incorporated by reference herein. The preparation of monoclonal antibody L6 is described briefly below.

Monoclonal antibodies were produced by immunizing three-month-old BALB/c mice with explanted cells from a human adenocarcinoma of the lung, 2981. The immunization was performed by injecting the mice intraperitoneally 4 times with approximately $10^7$ cells Three days after the last immunization, the spleens were removed, suspended in culture medium and fused with NS-1 mouse myeloma cells (Kohler and Milstein, 1975, Nature 256: 495-497). The mixtures were seeded to form low density cultures originating from single fused cells (clones); the techniques used for the hybridization have been previously described by Yeh et al., (1982, Int. J. Cancer 29: 269-275).

Supernatants from hybrid cells were screened by using both an ELISA assay and an autoradiographic indirect $^{125}$I-labeled protein A assay (Brown et al., 1979, J. Immunol. Meth. 31: 201-209) against extracts from the tumors used for These extracts were prepared using a procedure modified from Colcher et al. (1981, Cancer Res. 41: 1451-1459; Yeh et al., 1982, Int. J. Cancer 29: 269-275). To prepare the extracts tissues were washed and suspended with PBS; for intact tumors this was done by pressing through a stainless steel screen. After this, lmM $NaHCO_3$ containing 1 mM phenylmethylsulfonylfluoride (Calbiochem-Behring Corp., San Diego, Calif.) was added, and the material was then homogenized on ice. After centrifugation for 15 minutes at $27,000 \times g$, the supernatant was removed, and the pellet was resuspended in PBS, sonicated for 1 minute, and stored at $-70°$ C.

Hybridomas which produced antibodies binding to the cell membrane extracts were cloned, expanded in vitro, and further tested for antibody specificity. This testing was carried out by using an immunohistological technique (Garrigues et al., 1982, Int. J. Cancer, 29: 511-515), in which the ability of the antibodies to bind to frozen sections of lung carcinomas, other tumors and normal human tissues were tested. Those hybridomas which produced antibody of apparent specificity for human lung cancer were recloned, expanded and injected into pristane-primed three-month old BALB/c mice, where they grew as ascites tumors.

Antibodies secreted into the ascites were purified on protein A Sepharose (Ey et al., 1979, Immunochemistry, 15: 429-436) or by gel filtration in Sephacryl S-300. Purified antibodies were used for further characterization which included additional specificity tests by immunohistology, binding assays on intact cells to determine which antibodies bound to the cell surface, and by radioimmunoprecipitation tests.

Monoclonal antibody L6 was produced from the corresponding hybridoma as described above.

TUMOR THERAPY WITH COMBINATIONS OF BIOLOGICALLY ACTIVE ANTI-TUMOR ANTIBODIES AND CHEMOTHERAPY

The present invention provides for combination therapy comprising treatment with anti-tumor antibody as well as treatment with a standard chemotherapy regimen. In preferred embodiments of the invention, chemotherapy is administered concurrently with or, more preferably, subsequent to antibody therapy.

The antibodies utilized in the invention are preferably anti-glycolipid antibodies. In particular embodiments of the invention, it is desirable to utilize whole antibody molecules, whereas in alternative embodiments it will be desirable to use fragments of antibody molecules including but not limited to Fv, F(ab) and F(ab)$_2$ fragments. Such fragments can bind to tumor cells and render said cells more susceptible to chemotherapeutic agents while minimizing immune functions related to the Fc region of the antibody molecule and minimizing the generation of an immune response directed at a heterologous Fc region. Alternatively, it may be desirable to engineer monoclonal antibodies to comprise human Fc regions so as to maximize immune functions related to the Fc region. Accordingly, the present invention permits tailoring antibody therapy to better conform to individual clinical situations.

The chemotherapeutic regimens utilized according to the invention include any regimen believed to be suitable for the treatment of a patient's malignancy. Different malignancies can require the use of specific anti-tumor antibodies and specific chemotherapy regimens, which will be determined on a patient to patient basis. The present invention relates to any malignant condition, including, but not limited to, adenocarcinomas such as breast carcinoma and colon carcinoma, non-small cell lung carcinoma, leukemia, lymphoma and neuroectoderm derived tumors including melanoma, astrocytoma and glioblastoma.

The use of anti-tumor antibody therapy and chemotherapy combination treatment is exemplified in Sections 5, 6, and 7 infra. Notably, the melanoma patient discussed in Section 7 showed complete remission of extracranial tumors but died from an intracranial metastasis which did not respond to treatment. This lack of response of the brain metastasis may be explained by a failure of antibody to penetrate the blood-brain barrier. According to the invention it is desirable to ensure that the anti-tumor antibody is capable of contacting its tumor cell target. Therefore, in patients bearing tumors which are relatively inaccessible to exogenously administered antibodies, including brain tumors, it can be desirable to either administer antibodies locally into the tumor or, in the case of brain tumors, to render the blood brain barrier more permeable, for example with an osmotic agent, or to administer antibody or antibody fragments into the cerebrospinal fluid or via the carotid artery.

EXAMPLE: A BREAST CANCER PATIENT PREVIOUSLY UNRESPONSIVE TO THERAPY ACHIEVED COMPLETE REMISSION AFTER COMBINATION THERAPY

K. L. is a 46 year old white female who had a lumpectomy and axillary dissection in 1985 for Stage I, estrogen receptor negative breast cancer. She received local radiotherapy post operatively. She relapsed two years later with a nodule in the left axilla outside the radiation field. She received six months of chemotherapy with adriamycin, 5-fluorouracil, and cyclophosphamide (FAC). Five months later she relapsed with extensive disease in the remaining breast. She had a mastectomy, but again relapsed within three months. She was treated with Vinblastine/Mitomycin C but had progressive disease on her left chest wall. Because this patient displayed broad spectrum drug resistance and developed a rapid recurrence, her physician felt that additional chemotherapy was unlikely to be successful. The patient was referred for alternative treatments.

After evaluating the patient, it was found that she also displayed drug resistant disease, and it was unlikely that additional response would occur with chemotherapy. She was treated with murine monoclonal antibody L6 for seven days. She had an excellent response and two months later was in a complete remission with the complete disappearance of the disease on her chest wall. This remission was short lived and she recurred about two months later. Because of her previous good response to antibodies, she was retreated. There was no response, and her disease continued to rapidly progress. Because of her progression, she was started on alternative chemotherapy after four months. She received Mitomycin C, VP-16, carboplatinum, and 5-FU. It was felt unlikely that she would respond to these drugs because she had received two of them previously and had progressed. The patient was seen six weeks later and at that time, she had had a complete clearing of the disease from her chest wall. She was determined to be in a complete remission at that time. She was seen again ten weeks later, and continued to be in a complete remission.

This response to chemotherapy was unexpected and quite dramatic. The patient had displayed drug resistant disease and indeed had progressed on similar combination chemotherapy. It was unusual that she had such a dramatic prolonged response to treatment. It is speculated that there was some synergy between monoclonal antibody treatment and the chemotherapy. It is theorized that the antibodies induced the tumor cells to become sensitive to chemotherapy, whereas they had previously been totally resistant. An alternative hypothesis is that the antibodies induced a subtherapeutic immunological response. By itself, this would be inadequate to cause tumor regression, however, the addition of chemotherapy caused enough cellular disruption that tumor regression occurred.

EXAMPLE: A BREAST CANCER PATIENT PREVIOUSLY RESPONSIVE TO ANTIBODY THERAPY BUT IN RELAPSE ACHIEVED COMPLETE REMISSION AFTER COMBINATION THERAPY

M.G. is a 39 year old white female who was diagnosed as having inflammatory breast cancer. She was initially treated with cyclophosphamide/Adriamycin/tamoxifan/Premarinmethotrexate/5-FU and leucovorin. This was followed by a mastectomy which showed persistent extensive disease in the breast. Estrogen receptors and progesterone receptors were negative. There were multiple positive axillary nodes. Post operatively, she received radiation therapy to the chest wall and four additional cycles of chemotherapy. She progressed while receiving this chemotherapy. Because of the rapid progression and obvious drug resistance of this patient's tumor, she was referred for alternative treatment.

The patient received murine monoclonal antibody L6. She tolerated this treatment well, but continued to develop rapidly progressing disease on her chest wall. Three months after L6 therapy, she developed a malignant pleural effusion. She was treated with Mitomycin C and Vinblastine. Over the next six months there was a dramatic decrease in her tumor nodules and a disappearance of her pleural effusion. She has exhibited essentially a complete response to this chemotherapy.

As in the patient described in Section 5, supra, the response of this patient to chemotherapy was unexpected and dramatic. She had progressed on first-line chemotherapy using the best of six drugs available. It would be extremely unusual for her to respond to third-line drugs such as Vinblastine and Mitomycin C. As in the patient described in Section 5, it appears that there was some synergism between the use of monoclonal antibodies and chemotherapy.

EXAMPLE: A MELANOMA PATIENT ACHIEVED COMPLETE REMISSION AFTER COMBINATION THERAPY

C. H. is a 65 year old white male who had a primary melanoma in his right middle calf. He developed recurrence in his right thigh two years later and underwent a right groin dissection and a local perfusion of his leg with melphalan. He did well for about 37 months when he again developed a nodule in his right groin. This was removed and found to be recurrent melanoma. He then developed multiple other nodules on his right lower extremity. When seen he had multiple nodules on his right lower extremity. He was diagnosed to have relatively slowly progressive disease which is not unusual for melanoma. He received high-dose Vitamin A for five months when it was determined he was obviously progressing. Treatment was continued for an additional 3 months after which he received monoclonal antibodies (MG21) for seven days. He tolerated these treatments well and had a slow response with a disappearance of his multiple subcutaneous nodules. Four months later the patient was felt to have a complete response to the monoclonal antibodies. He did well for nine months, when he relapsed. He was retreated with 1 mg of monoclonal antibody (MG21). He did not respond and his disease continued to progress. Four and one-half months later because of increasing disease, he again received a 7 day course of treatment with monoclonal antibodies. He did not respond and continued to rapidly progress with increasing nodules in his right lower extremity. After an additional four months he was started on PEG-IL2, another form of immunotherapy. He received four treatments with this, but again continued to progress. Because of the large tumors on his legs which started to erode through the skin and caused local pain, the patient had a surgical resection of numerous lesions. He continued to progress and was started on chemotherapy with DTIC/Cis-platinum/cimetidine/tamoxifen. He received 3 cycles of this chemotherapy and had a dramatic response with a complete disappearance of all the tumor nodules on his right lower extremities. This response again was somewhat dramatic. Response rates to melanoma average around 30–40% with complete responses of less than 5%. The response durations are usually less than 6 months. This patient had a dramatic response with the disappearance of rather bulky disease. As in patients K. L. and M.G. (supra), this was a more dramatic response than one would expect to see. The patient did well for over one year when he developed brain metastases. He had surgery and local radiation therapy, but had a slow downhill course and subsequently died. At the time of his death, he had no evidence of melanoma outside of the brain.

This occurrence of relapse of melanoma in his brain while free of disease peripherally should not be viewed as a failure of chemotherapy. Most chemotherapy drugs, as well as antibodies, do not enter the central nervous system. It is considered as a sanctuary for most treatment. The fact that his disease was in remission outside the central nervous system confirms that there was a dramatic biological response at these sites.

DEPOSIT OF CELL LINES

The MG21 and L6 cell lines have been deposited with the American Type Culture Collection, 12301 Parklawn Drive Rockville Md., 20852, on Feb. 4, 1986 and Dec. 6, 1984, respectively, and have been assigned the following accession numbers:

| Cell Line | Accession Number |
|---|---|
| MG21 | HB 9011 |
| L6 | HB 8677 |

The present invention has been described in detail with particular reference to the above embodiments. It will be understood, however, that the present invention is not to be limited in scope by the embodiments disclosed or cell lines deposited which are intended as illustrations of aspects of the invention.

Indeed, various modifications of the invention in addition to those shown and described herein will become apparent to those skilled in the art from the foregoing description. Such modifications are intended to fall within the scope of the appended claims.

What is claimed is:

1. A method of treating a patient who has breast carcinoma and who has previously demonstrated an unresponsiveness to standard chemotherapy regimens, comprising: (a) first administering to that patient monoclonal antibody L6 produced by hybridoma ATCC HB 8677, and (b) followed by administration of a chemotherapeutic agent.

2. A method of treating a patient who has melanoma and who has previously demonstrated an unresponsivenss to standard chemotherapy regimens, comprising: (a) first administering to that patient monoclonal antibody MG21 produced by hybridoma ATCC HB 9011, and (b) followed by administration of a chemotherapeutic agent.

* * * * *